United States Patent
Stoimenov et al.

(10) Patent No.: US 9,771,308 B2
(45) Date of Patent: Sep. 26, 2017

(54) PRODUCTION OF 1,3-BUTADIENE

(71) Applicant: REACTION 35, LLC, Santa Barbara, CA (US)

(72) Inventors: Peter K. Stoimenov, Goleta, CA (US); Jeffrey H. Sherman, Vero Beach, FL (US)

(73) Assignee: REACTION 35, LLC, Houston, TX (US)

( * ) Notice: Subject to any disclaimer, the term of this patent is extended or adjusted under 35 U.S.C. 154(b) by 153 days.

(21) Appl. No.: 14/734,683

(22) Filed: Jun. 9, 2015

(65) Prior Publication Data

US 2015/0361008 A1 Dec. 17, 2015

Related U.S. Application Data

(60) Provisional application No. 62/011,252, filed on Jun. 12, 2014.

(51) Int. Cl.
| | |
|---|---|
| *C07C 1/30* | (2006.01) |
| *C07C 17/10* | (2006.01) |
| *C07C 5/23* | (2006.01) |
| *C07C 5/25* | (2006.01) |

(52) U.S. Cl.
CPC ............ *C07C 1/30* (2013.01); *C07C 5/23* (2013.01); *C07C 5/2512* (2013.01); *C07C 5/2518* (2013.01); *C07C 17/10* (2013.01); *C07C 2521/06* (2013.01); *C07C 2521/08* (2013.01); *C07C 2521/10* (2013.01); *C07C 2527/22* (2013.01); *C07C 2527/224* (2013.01); *C07C 2529/035* (2013.01); *C07C 2529/04* (2013.01)

(58) Field of Classification Search
CPC ....... C07C 17/358; C07C 21/14; C07C 17/02; C07C 19/075; B01J 19/0066; B01J 19/18; B01J 2219/00094; B01J 2219/00103; B01J 2219/0011; B01J 2219/00159; B01J 2219/00779; B01J 2219/185

See application file for complete search history.

(56) References Cited

U.S. PATENT DOCUMENTS

| | | | |
|---|---|---|---|
| 2,913,502 A | 11/1959 | Elian et al. | |
| 3,246,043 A * | 4/1966 | De Rosset | C07C 1/30 585/318 |
| 3,962,357 A | 6/1976 | Merritt et al. | |
| 4,039,598 A * | 8/1977 | Uriarte | B01J 27/08 570/204 |
| 7,883,568 B2 | 2/2011 | Gadewar et al. | |
| 8,680,350 B2 * | 3/2014 | Hatscher | B01J 23/80 585/258 |
| 8,940,954 B2 | 1/2015 | Julka et al. | |
| 2012/0302808 A1 * | 11/2012 | Julka | C07C 1/30 585/324 |

OTHER PUBLICATIONS

International Search Report and Written Opinion issued in International Application No. PCT/US2015/034904, dated Aug. 21, 2015 (11 pages).

* cited by examiner

*Primary Examiner* — Sharon Pregler
(74) *Attorney, Agent, or Firm* — Adolph Locklar (57) ABSTRACT

Olefins and diolefins, such as 1,3-butiadiene, may be produced by a method utilizing a series of bromination and dehydrobromination reactions. Bromine may be reacted with n-butane to form dibromobutane. The dibromobutanes may be dehydrobrominating to form 1,3-butadiene. The method may include reacting butene with bromine to form bromobutenes, and dehydrobrominating the bromobutenes to form 1,3-butadiene. The method may include reacting butene with hydrogen bromide in the presence of oxygen to form bromobutenes, and dehydrobrominating the bromobutenes to form 1,3-butadiene. The method may include reacting butene with bromine to form dibromobutanes, and dehydrobrominating the dibromobutanes to form 1,3-butadiene.

28 Claims, 7 Drawing Sheets

PRODUCTION OF 1,3-BUTADIENE

CROSS-REFERENCE TO RELATED APPLICATIONS

This application is a non-provisional application which claims priority from U.S. provisional patent application No. 62/011,252, filed Jun. 12, 2014, which is incorporated by reference herein in its entirety.

FIELD

The present disclosure generally relates to methods of producing olefins and diolefins utilizing halogenation and dehydrohalogenation. In particular, the present disclosure relates to methods of producing 1,3-butadiene from n-butane or butenes utilizing bromination and dehydrobromination.

BACKGROUND

Conventionally, one method of obtaining 1,3-butadiene is by extraction from a crude $C_4$ stream produced as a co-product of steam cracking. Because 1,3-butadiene has physical properties that are close to other $C_4$ species in such crude $C_4$ streams, extractive distillation is often utilized to separate 1,3-butadiene from the other $C_4$ species. Such extractive distillations typically utilize solvents, such as N-methylpyrrollidone or acetone.

Another conventional method of obtaining 1,3-butadiene is by dehydrogenation of n-butane and butenes. For example, 1,3-butadiene may be prepared industrially by the so-called CATADIENE® (Houdry) process. Such a process generally involves dehydrogenation of n-butane or 1-butene and 2-butenes over a fixed or fluidized catalyst.

Additionally, 1,3-butadiene may be obtained by conversion of ethanol. For example, 1,3-butadiene may be produced by the Lebedev method, in which ethanol is converted catalytically to 1,3-butadiene. Such methods generate byproducts including hydrogen and water.

SUMMARY

The present disclosure provides for a method. The method includes reacting n-butane with bromine in one or more bromination reactors to form a bromination product stream containing dibromobutane. The method further includes subjecting the dibromobutane to dehydrobromination in a dehydrobromination reactor to form a dehydrobromination product stream containing 1,3-butadiene.

The present disclosure provides for a method. The method includes reacting butene with bromine in a bromination reactor under reaction conditions adapted for selective bromination of the butene in the allylic position to form a bromination product stream containing bromobutenes. The method includes subjecting the bromobutenes to dehydrobromination in a dehydrobromination reactor to form a dehydrobromination product stream containing 1,3-butadiene.

The present disclosure provides for a method. The method includes reacting butene with hydrogen bromide in the presence of oxygen in an oxybromination reactor under reaction conditions sufficient to cause oxybromination of the butenes to form an oxybromination product stream containing bromobutenes. The method includes subjecting the bromobutenes to dehydrobromination in a dehydrobromination reactor to form a dehydrobromination product stream containing 1,3-butadiene.

The present disclosure provides for a method. The method includes reacting butene with bromine in a bromination reactor to form a bromination product stream containing dibromobutanes. The method includes subjecting the dibromobutanes to dehydrobromination in a dehydrobromination reactor to form a dehydrobromination product stream containing 1,3-butadiene.

BRIEF DESCRIPTION OF THE DRAWINGS

The present disclosure is best understood from the detailed description when read with the accompanying figures. In accordance with the standard practice in the industry, various features are not drawn to scale.

DETAILED DESCRIPTION

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure generally relates to methods of producing olefins and diolefins utilizing halogenation reactions and dehydrohalogenation reactions. The olefins and diolefins may be produced from alkanes, for example. The method may include halogenation of the alkane, forming alky halides and hydrogen halide, followed by dehydrohalogenation of the alky halides, forming olefins and diolefins and hydrogen halide. The hydrogen halide may subsequently be reacted with oxygen, forming water and the halogen.

In certain embodiments, the alkane is a $C_4$ alkane and the diene is a $C_4$ diene. For example, the alkane may be n-butane and the diene may be 1,3-butadiene or 1,2-butadiene. In some embodiments, the halogen is bromine. While the reaction sequences discussed herein utilize bromine as the halogen, n-butane as the alkane, and 1,3-butadiene or 1,2-butadiene as the alkene, one skilled in the art with the aid of the present disclosure would understand that the method may be applied to other alkanes, halogens, alkenes, dienes and alkynes.

The method may exhibit high carbon efficiency, that is, the method may include only a small amount of carbon loss due to coking or incineration of undesired byproducts. In particular, the method may exhibit a carbon loss of below 10 wt. %, or below 8 wt. %, or below 5 wt. % of the starting butane.

Certain embodiments disclosed herein relate to a method of producing a diene (e.g. 1,3-butadiene) from an alkane (e.g, n-butane). The method may include dehydrogenation of the alkane to form the diene. The dehydrogenation of the alkane to form the diene may be accomplished indirectly through a series of halogenation-dehydrohalogenation reactions. In embodiments in which the halogen is bromine, the dehydrogenation of the alkane to the diene may be accomplished indirectly through a series of bromination-dehydrobromination reactions. Hydrogen halide (e.g., hydrogen bromide) is produced as a byproduct of the halogenation-dehydrohalogenation reaction sequence. In some embodiments, the hydrogen halide may be oxidized to form the corresponding halogen (e.g., bromine) for reuse in the bromination reaction.

An exemplary reaction sequence in accordance with certain embodiments for the dehydrogenation of n-butane to 1,3-butadiene is shown in Reaction Sequence A, including reactions (1)-(5). In Reaction Sequence A, the halogen is bromine, the alkane is n-butane, and the diene is 1,3-butadiene; however, one skilled in the art with the aid of the present disclosure would understand that the method may be applied to other alkanes, halogens, alkenes, dienes and alkynes.

Reaction Sequence A:

$$CH_3—CH_2—CH_2—CH_3+Br_2 \rightarrow CH_3—CH_2CH(Br)—CH_3+HBr \quad (1)$$

$$CH_3—CH_2CH(Br)—CH_3+Br_2 \rightarrow BrCH_2—CH_2—CH(Br)—CH_3+HBr \quad (2)$$

$$BrCH_2—CH_2—CH(Br)—CH_3 \rightarrow CH_2=CH—CH=CH_2+2HBr \quad (3)$$

$$4HBr+O_2 \rightarrow 2H_2O+2Br_2 \quad (4)$$

Overall: $CH_3—CH_2—CH_2—CH_3+O_2 \rightarrow CH_2=CH—CH=CH_2+2H_2O \quad (5)$

Thus, Reaction Sequence A includes a step of bromination of n-butane to form monobromobutanes, which may include 1-bromobutane or 2-bromobutane. Reaction Sequence A further includes a step of bromination of the monobromobutanes to form dibromobutanes. The dibromobutanes are then dehydrohalogenated to form 1,3-butadiene and hydrogen bromide. The hydrogen bromide is then reacted with oxygen to form water and bromine.

Bromination

In certain embodiments, the method includes introduction of one or more double bonds into an alkane (e.g., n-butane). The method may include halogenation (e.g., bromination) of the alkane. Halogenation of the alkane results in the substitution of a halogen atom for a hydrogen atom in the structure of the alkane, thus forming an alkyl halide, such as mono- or di-bromobutane. The thus formed alkyl halide is then dehydrohalogenated to form an alkene (e.g. 1,3-butadiene).

In certain embodiments, only one double bond is introduced into the alkane to form a mono-alkyl halide, followed by dehydrohalogenation of the mono-alkyl halide to generate a corresponding alkene.

In certain embodiments, multiple double bonds may be introduced into the alkane by substituting additional halogen atoms for hydrogen atoms on the alkane, followed by dehydrohalogenating the alkyl halide.

The bromination reactions disclosed herein may occur at temperatures above 150° C. At temperatures above 450° C., the bromination reaction may produce unacceptable levels of coke. In certain embodiments, the bromination reactions disclosed herein may occur at temperatures between 200° C. and 450° C., or between 200° C. and 375° C.

As described in more detail below, bromination of an alkane may occur by simultaneous double bromination or sequential bromination. The method may include reacting n-butane with bromine in one or more bromination reactors to form a bromination product stream that contains dibromobutanes. The dibromobutanes may then be subjected to dehydrobromination in a dehydrobromination reactor to form a dehydrobromination product stream that contains 1,3-butadiene. In some embodiments, the one or more bromination reactors include only one bromination reactor (i.e., simultaneous double bromination), and the n-butane is subjected to double bromination in the one bromination reactor. In some embodiments, the one or more bromination reactors include a first bromination reactor and a second bromination reactor (i.e., sequential bromination). The second bromination reactor may be downstream of the first bromination reactor. The n-butane may react with bromine in the first bromination reactor to form monobromobutanes, and the monobromobutanes may react with additional bromine in the second bromination reactor to form dibromobutanes.

As described in more detail below, bromination may occur by simultaneous double bromination of an alkane, sequential bromination of an alkane, allyl bromination of an alkene, oxybromination of an alkene, or bromination of an alkene to produce a dibromoalkane, for example.

Single Step Double Bromination

In certain embodiments, halogenation of the alkane may be performed by single step double halogenation. In single step double halogenation, two hydrogens of the alkane are substituted by two halogens in a single step, such as in a single reaction zone or single reactor. For the purposes of brevity and clarity, a single step double bromination of n-butane is described herein with reference to FIG. 1, however, one skilled in the art with the aid of the present disclosure would understand that the single step double halogenation may be applied using other alkanes and/or halogens.

Figure 1:
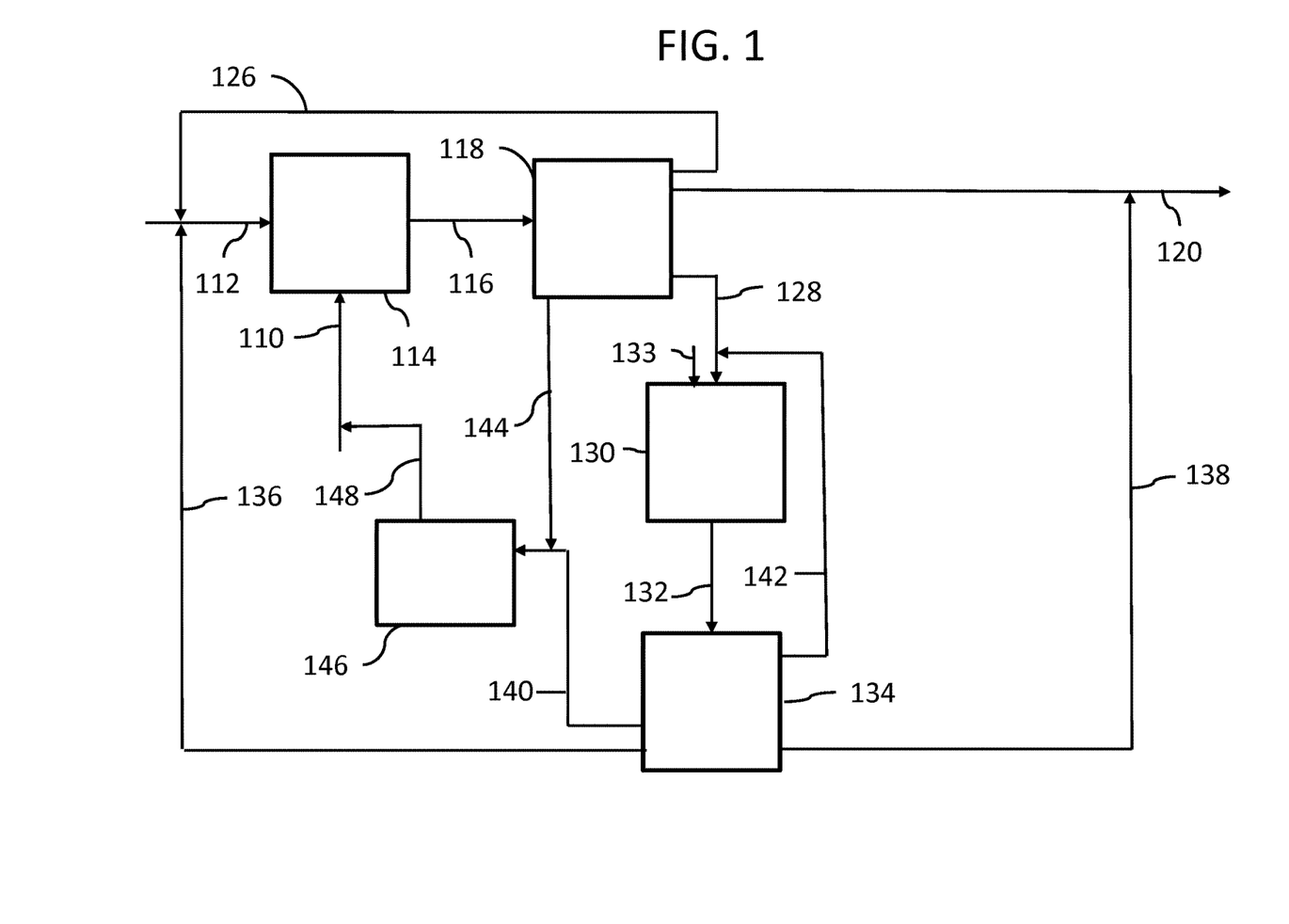
FIG. 1 is a process flow diagram depicting simultaneous double bromination of n-butane in accordance with one or more embodiments of the present disclosure.

In single step double bromination, n-butane 112 may be converted to a double brominated alkane (i.e., dibromobutanes 120). Bromine 110 may be reacted with n-butane 112, such as in bromination reactor 114, to form bromination product stream 116. Bromination product stream 116 may include butyl bromides, dibromobutanes, polybromobutanes, hydrogen bromide, unreacted butane, or combinations thereof, for example. Bromine 110 is reacted with n-butane 112 at a molar ratio of bromine 110 to n-butane 112 and under reaction conditions (e.g., temperature and pressure) that maximizes the yield of dibromobutanes, and that minimizes the formation of tri-, tetra- and higher bromobutanes, also referred to herein as polybromobutanes. Single step double bromination may be performed at a molar ratio of bromine to alkane of 0.5 to 1.7, such as 1.3. Single step double bromination may be performed at elevated temperatures in the range of 150-400° C., or at 300-350° C. The yield of dibromobutanes may contain one or more isomers, including 1,3-dibromobutane, vicinal dibromides, geminal dibromides, or combinations thereof.

In some embodiments, the single step double bromination may be performed in the presence of a catalyst adapted to facilitate the selectivity of desirable dibromobutane isomers in the single step double bromination reaction. For example and without limitation, the catalyst may be a highly polar surface catalyst such as silica, glass, silicalite, quartz chips, zirconia or titania. Such highly polar catalysts may increase the ratio of 1,3-dibromobutane to the vicinal and geminal dibromobutane isomers in bromination product stream 116. In some embodiments, the single step double bromination may be performed in the absence of a catalyst, i.e., the single step double bromination may be thermally induced.

In certain embodiments, after single step double bromination, the method may include separation of bromination product stream 116 into one or more streams of butyl bromides, dibromobutanes, polybromobutanes, hydrogen bromide, unreacted butane, or combinations thereof. The separation of the bromination product stream 116 may be performed in separator 118 by any suitable method known to those skilled in the art. For example and without limitation, bromination product stream 116 may be separated by distillation.

The separation of bromination product stream 116 may form a stream containing dibromobutanes 120. The stream containing dibromobutanes 120 may be enriched in dibromobutane, that is, the stream containing dibromobutanes 120 may include a proportion of dibromobutanes by weight percent that is increased relative to the proportion of dibromobutanes in bromination product stream 116. Dibromobutanes 120 obtained from the simultaneous double bromination reaction may be then subjected to dehydrobromination, as described in more detail below, to generate a dehydrobromination product stream that includes butadienes. In some embodiments, dehydrobromination of dibromobutanes 120 produces 1,3-butadiene; 1,2-butadiene; and butynes. The butynes may include 1-butyne, also known as ethylacetylene, and 2-butyne, also known as dimethylacetylene. Optionally, the 1,2-butadiene and butynes may be isomerized to 1,3-butadiene.

The separation of bromination product stream 116 may form stream 126 containing the unreacted butane, butyl bromides, or both. Stream 126 may be enriched in unreacted butane, butyl bromides, or both, that is, stream 126 may include a proportion of unreacted butane, butyl bromides, or both by weight percent that is increased relative to bromination product stream 116. Stream 126 may be recycled to the single step double bromination reaction. For example and without limitation, stream 126 may be combined with n-butane 112 upstream of bromination reactor 114.

The separation of bromination product stream 116 may form a stream containing polybromobutanes 128 obtained from the simultaneous double bromination reaction. The stream containing polybromobutanes 128 may be enriched in polybromobutanes, that is, the stream containing polybromobutanes 128 may include a proportion of polybromobutanes by weight percent that is increased relative to bromination product stream 116. Polybromobutanes 128 may be subjected to hydrogenation in the presence of hydrogen 133, such as in hydrogenation reactor 130. The reaction conditions (e.g., temperature and pressure) utilized in the hydrogenation of polybromobutanes 128 may be selected to maximize the yield of dibromobutanes. Hydrogenation of polybromobutanes 128 may be performed in the presence of a catalyst, such as nickel, palladium or platinum. Hydrogenation of polybromobutanes 128 may form product stream 132 that includes butane, butyl bromide, dibromobutanes, HBr, polybromobutanes, or combinations thereof.

Following hydrogenation of polybromobutanes 128, product stream 132 may be separated, such as in separator 134. For example and without limitation, product stream 132 may be separated by distillation. Separation of product stream 132 may form first stream 136 enriched in butane, butyl bromide, or combinations thereof; second stream 138 enriched in dibromobutanes; third stream 140 enriched in HBr; fourth stream 142 enriched in polybromobutanes; or combinations thereof. The dibromobutanes of second stream 138 may be combined with dibromobutanes 120 recovered from the simultaneous double bromination, and subsequently subjected to dehydrobromination to generate butadienes as described herein. The butane and butyl bromides of first stream 136 may be recycled and combined with n-butane 112 upstream of bromination reactor 114. The polybromobutanes of fourth stream 142 may be recycled to hydrogenation reactor 130. For example, the polybromobutanes of fourth stream 142 may be combined with polybromobutanes 128 recovered from the single step double bromination reaction, and then sent to hydrogenation reactor 130.

The separation of bromination product stream 116 may form a stream containing hydrogen bromide 144. The stream containing hydrogen bromide 144 may be enriched in hydrogen bromide, that is, the stream containing hydrogen bromide 144 may include a proportion of hydrogen bromide by weight percent that is increased relative to bromination product stream 116. Hydrogen bromide 144 obtained from the simultaneous double bromination reaction, the hydrogen bromide of third stream 140 obtained from hydrogenation of polybromobutanes 128, or combinations thereof may be sent to oxidation reactor 146 in which bromine 148 is regenerated for use in the simultaneous double bromination reaction. For example, bromine 148 (elemental) may be recycled and combined with bromine 110 upstream of the bromination reactor 114. Oxidation of hydrogen bromide also forms water (not shown), and is discussed in more detail below with respect to FIG. 7.

Sequential Bromination

In certain embodiments, halogenation of the alkane may be performed by sequential halogenation. For the purposes of brevity and clarity, sequential bromination of n-butane is described herein with reference to FIGS. 2A and 2B, however, one skilled in the art with the aid of the present disclosure would understand that the sequential halogenation may be applied using other alkanes and/or halogens.

Figure 2A:
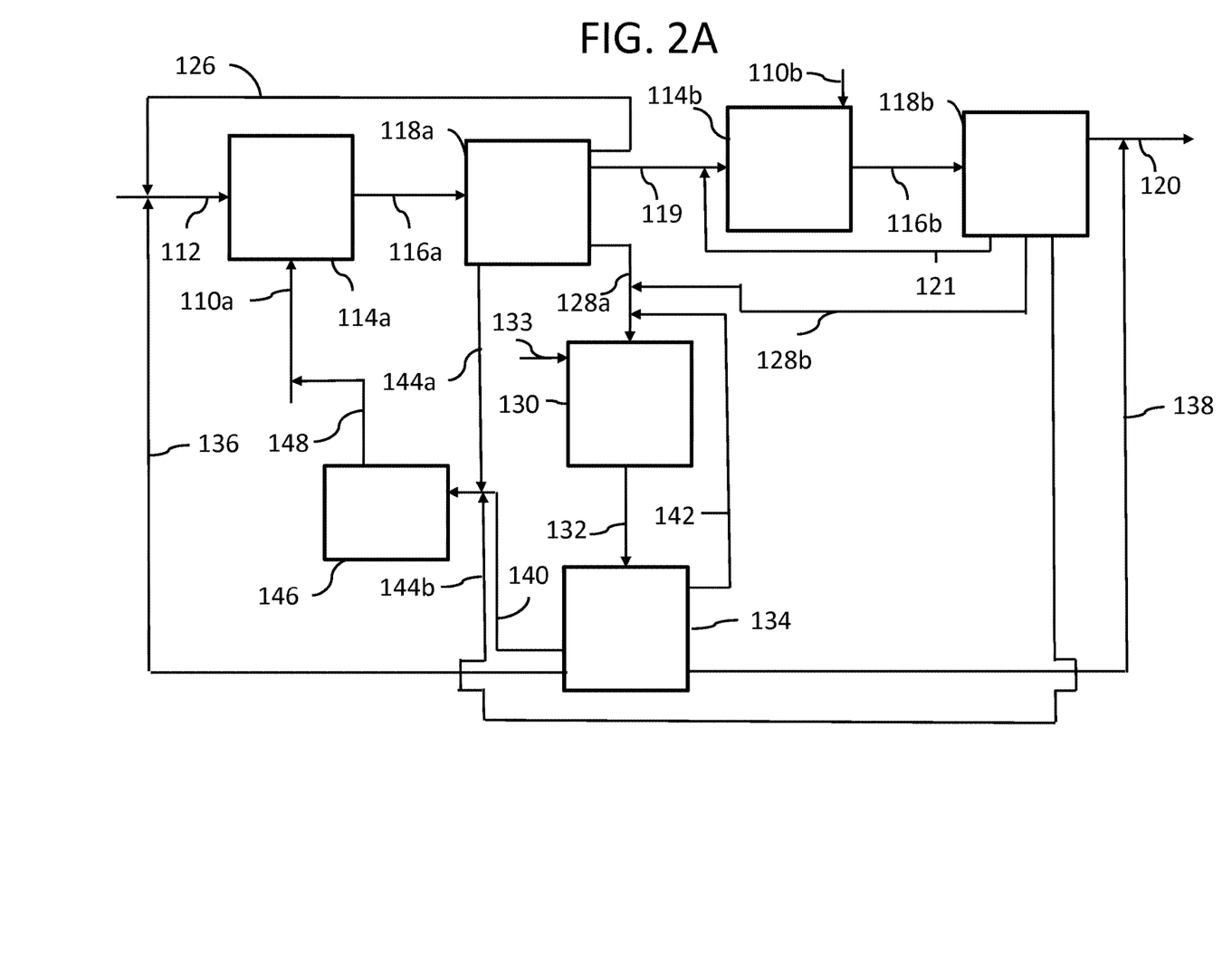
FIG. 2A is a process flow diagram depicting sequential bromination of n-butane with an intermediate separation in accordance with one or more embodiments of the present disclosure.

Sequential bromination may include two sequential bromination steps. In certain embodiments, sequential bromination includes only two sequential bromination steps. In a first bromination reaction of the sequential bromination, n-butane 112 is reacted with bromine 110a, such as in first bromination reactor 114a. In the first bromination reaction, a molar ratio of bromine 110a to n-butane 112 and the reaction conditions (e.g., temperature and pressure) are selected to maximize the yield of monobromobutanes in bromination product stream 116a. For example and without limitation, a molar ratio of $Br_2$/n-butane may range from less than 0.4 to 1.7, such as 0.5. The temperature may range from 200-400° C., such as 300° C. The residence time may range from 5 seconds to 15 seconds, such as 10 seconds. In the first bromination reaction, the butane conversion may range from 30 to 50%, or 35 to 45%, or about 41.7%, for example.

The monobromobutanes in bromination product stream 116a include 1-bromobutane, 2-bromobutane, or combinations thereof. Bromination product stream 116a may then be separated, such as in separator 118a. Separation of bromination product stream 116a may be performed by distillation, for example. Separation of bromination product stream 116a may form a stream enriched in monobromobutanes (i.e., a stream containing bromobutanes 119).

Separation of bromination product stream 116a may form hydrogen bromide 144a, polybromobutanes 128a, and stream 126 containing the unreacted butane, butyl bromides, or both, as described above with respect to FIG. 1. Stream 126 may be recycled upstream to combine with n-butane 112, polybromobutanes 128a may be sent to hydrogenation reactor 130, and hydrogen bromide 144a may be sent to oxidation reactor 146.

The stream containing bromobutanes 119 may be recovered from separator 118a. The recovered bromobutanes 119 may be subjected to a second, separate bromination reaction, such as in second bromination reactor 114b. For example and without limitation, bromobutanes 119 and a stream containing bromine 110b may be fed to second bromination reactor 114b, which may be operated under conditions for the selective bromination of the monobromobutanes in bromobutanes 119 to form bromination product stream 116b containing dibromobutanes. For example and without limitation, the temperature may range from about 200° C. to about 275° C., the residence time may range from about 4 to about 12 seconds or about 5 to about 10 seconds, and the molar ratio of bromine to bromobutane may range from about 0.2 to about 0.6, such as about 0.4. Utilization of sequential bromination allows for the use of different reaction conditions for each of the sequential bromination reactions. For example and without limitation, the first bromination reaction in bromination reactor 114a may be conducted without a catalyst (e.g., a thermal induced reaction), while the second bromination reaction in bromination reactor 114b is conducted in the presence of a catalyst adapted for the increased yield of the 1,3-dibromobutane isomer and minimized formation of polybromobutanes. Alternatively, the first bromination reaction in bromination reactor 114a may be conducted in the presence of a catalyst, while the second bromination reaction in bromination reactor 114b is performed without a catalyst. In some embodiments, the same reaction conditions are utilized in each bromination rector 114a and 114b of the sequential bromination.

Bromination product stream 116b may be separated, such as in separator 118b. Separation of bromination product stream 116b may be performed by distillation, for example. Separation of bromination product stream 116b may form a stream enriched in dibromobutanes 120, which may be subjected to dehydrobromination, as detailed below, to form butadienes. Separation of bromination product stream 116b may form a stream enriched in unreacted bromobutanes 121, which may be recycled to bromination reactor 114b, such as by being combined with bromobutanes 119 upstream of bromination reactor 114b.

Separation of bromination product stream 116b may form a stream enriched in polybromobutanes 128b. Polybromobutanes 128b may be subjected to hydrogenation in hydrogenation reactor 130 along with polybromobutanes 128a in the presence of hydrogen 133. Hydrogenation of polybromobutanes 128a and 128b may form product stream 132 that includes butane, bromobutanes, dibromobutanes, HBr, polybromobutanes, or combinations thereof.

Product stream 132 may be separated, such as in separator 134. For example and without limitation, product stream 132 may be separated by distillation. Separation of product stream 132 may form first stream 136 enriched in butane, bromobutanes, or combinations thereof; second stream 138 enriched in dibromobutanes; third stream 140 enriched in HBr; fourth stream 142 enriched in polybromobutanes; or combinations thereof. The dibromobutanes of second stream 138 may be combined with dibromobutanes 120 recovered from the sequential bromination, and subsequently subjected to dehydrobromination to generate butadienes as described herein. The butane and butyl bromides of first stream 136 may be recycled and combined with n-butane 112 upstream of bromination reactor 114a. The polybromobutanes of fourth stream 142 may be recycled to hydrogenation reactor 130. For example, the polybromobutanes of fourth stream 142 may be combined with polybromobutanes 128a and 128b, and then sent to hydrogenation reactor 130.

Separation of bromination product stream 116b may form a stream containing HBr 144b, which may be combined with hydrogen bromide 144a obtained from the first bromination reaction and the hydrogen bromide of third stream 140 obtained from hydrogenation of polybromobutanes 128a and 128b. Hydrogen bromide 144a and 144b and the hydrogen bromide of third stream 140 may be sent to oxidation reactor 146 in which bromine 148 is regenerated for use in the sequential bromination reaction. For example, bromine 148 may be combined with bromine 110a upstream of first bromination reactor 114a.

Figure 2B:
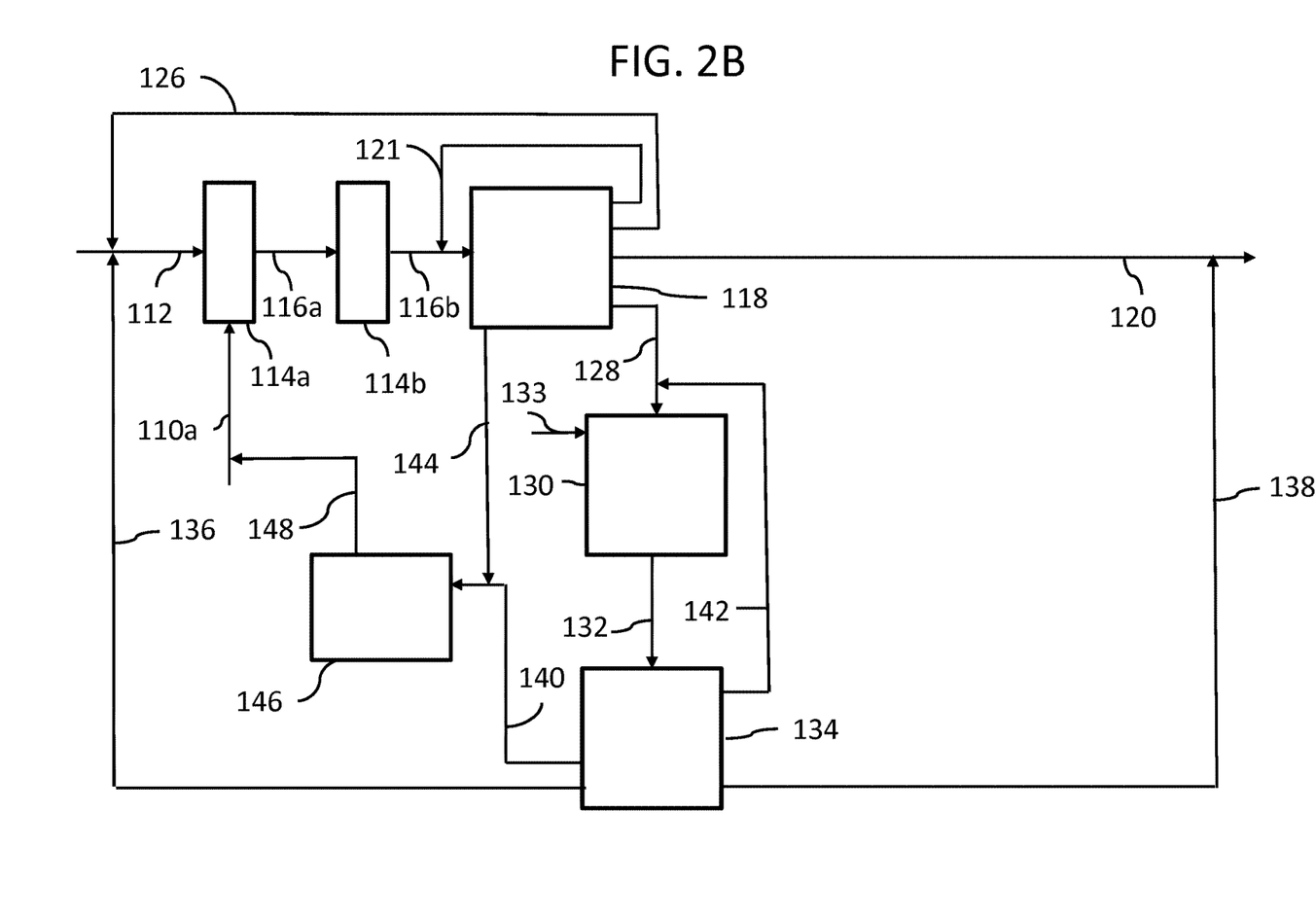
FIG. 2B is a process flow diagram depicting sequential bromination of n-butane without an intermediate separation in accordance with one or more embodiments of the present disclosure.

In certain embodiments, as depicted in FIG. 2B, sequential bromination is carried out without use of a separator between first bromination reactor 114a and second bromination reactor 114b. First bromination product stream 116a may be transferred from first bromination reactor 114a into second bromination reactor 114b without passing through a separator. For example and without limitation, first bromination product stream 116a may be transferred from first bromination reactor 114a directly into second bromination reactor 114b. As discussed above, the operating conditions in first bromination reactor 114a, including the molar ratio of bromine 110a to n-butane 112, reactor temperature and reactor pressure, may be selected to maximize the yield of bromobutanes. The operating conditions in second bromination reactor 114b may be selected to maximize the conversion of bromobutanes and yield of dibromobutanes. The separation of bromination product stream 116b in embodiments without use of a separator between first bromination reactor 114a and second bromination reactor 114b may be conducted in separator 118 in the same manner as described above with respect to separation of bromination product stream 116 in FIG. 1 to form streams dibromobutanes 120, polybromobutanes 128, hydrogen bromide 144 and stream 126. Hydrogen bromide 144 may be subjected to oxidation in oxidation reactor 146 to form bromine 148. Polybromobutanes 128 may be subjected to hydrogenation in the presence of hydrogen 133 to form products stream 132, which may be separated, such as by distillation, in separator 134 to form stream 138 enriched in dibromobutanes, stream 140 enriched in hydrogen bromide, stream 142 enriched in polybromobutanes, and stream 136 enriched in butane, butyl bromide, or combinations thereof. Stream 136 enriched in butane, bromobutanes, or combinations thereof may be recycled and combined with n-butane 112. Stream 140 may be subjected to oxidation in oxidation reactor 146 to form bromine 148. Stream 138 may be combined with dibromobutanes 120. Stream 142 may be recycled and combined with polybromobutanes 128 upstream of hydrogenation reactor 130 for hydrogenation in the presence of hydrogen 133.

Embodiments of sequential bromination that include the intermediate separation between first bromination reactor 114a and second bromination reactor 114b, as depicted in FIG. 2A, may exhibit increased selectivity toward the 1,3-dibromobutane isomer as compared to embodiments of sequential bromination that do not include the intermediate separation between first bromination reactor 114a and second bromination reactor 114b, as depicted in FIG. 2B. However, the complexity of the reactor systems and the number of separate chemical processes may be reduced for embodiments of sequential bromination that do not include the intermediate separation between first bromination reactor 114a and second bromination reactor 114b, as compared with embodiments of sequential bromination that do include the intermediate separation between first bromination reactor 114a and second bromination reactor 114b.

In certain embodiments, utilization of sequential bromination as exemplified in FIGS. 2A and 2B, as opposed to simultaneous double bromination as exemplified in FIG. 1, may improve selectivity towards the desired dibromobutanes.

Allyl Bromination of Butenes

In certain embodiments, bromoalkenes (e.g., bromobutenes) may be dehydrohalogenated (e.g., dehydrobrominated) to olefins and diolefins (e.g., butadienes). The bromoalkenes may be produced by selectively halogenating alkenes in the allylic position. For the purposes of brevity and clarity, allyl bromination of butenes is described herein with reference to FIG. 3, however, one skilled in the art with the aid of the present disclosure would understand that the method may be applied using other alkenes and/or halogens.

Figure 3:
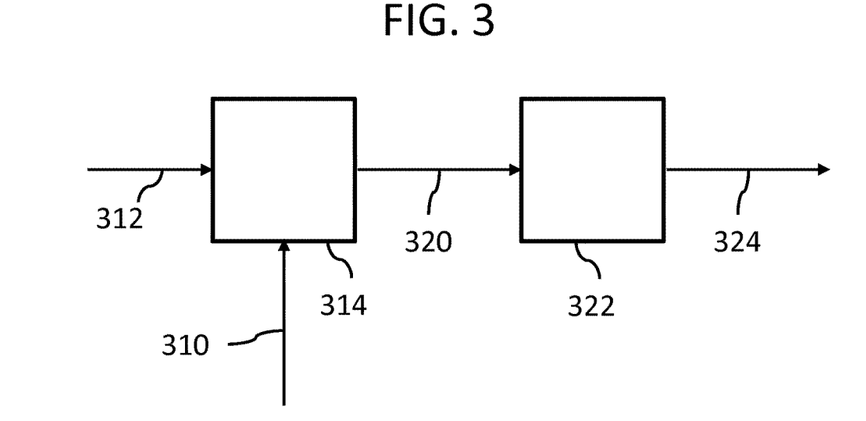
FIG. 3 is a process flow diagram depicting allyl bromination of butenes in accordance with one or more embodiments of the present disclosure.

The method may include reacting butenes 312 with bromine 310 in bromination reactor 314. For example and without limitation, bromobutenes 320 may be produced by selectively brominating butenes 312 in the allylic position in the presence of bromine 310. Bromobutenes 320 may then be dehydrobrominated to butadienes 324 in dehydrobromination reactor 322, as described in more detail below. While not shown, the product stream of bromination reactor 314 that contains bromobutenes 320 may be subjected to separation, such as by distillation, to form a stream enriched in bromobutenes 320 prior to dehydrobromination. In some embodiments, the method may include reacting butenes 312 with bromine 310 in a reactor, such as bromination reactor 314, to produce bromobutenes 320 by selectively brominating butenes 312 in the allylic position in the presence of bromine 310. Butadienes 324 may then be produced in situ within the same reactor by subjection of the bromobutenes 320 to dehydrobromination.

Butenes 312 may be produced through conventional means or, for example, through the catalytic dehydrobromination of bromobutanes to butenes as described in U.S. patent application Ser. No. 13/479,085, which is hereby incorporated by reference in its entirety. Butenes 312 may be preheated and mixed with preheated bromine 310 at temperatures exceeding 250° C., exceeding 275° C., equal to or less than 450° C., ranging from 250° C. to 450° C., ranging from 300° C. to 400° C., ranging from 250° C. to 325° C., ranging from 265° C. to 300° C., or ranging from 270° C. to 285° C. prior to reaction in bromination reactor 314. Under such conditions, the reaction mechanism is altered and bromine 310 substitutes an α-hydrogen on butenes 312, thus forming an allylic bromide, e.g. 2-butene may react to form 1-bromo-2-butene, and forming 3-bromo-1-butene, e.g., 1-butene may react to form 3-bromo-1-butene (see, Reaction (6)), instead of adding across the double bond which is the typical reaction between a halogen and an olefin (see, Reaction (7)). This is exemplified by Reaction (6), which was carried out at a temperature of greater than 250° C., and Reaction (7), which was carried out at room temperature, below 250° C.

(6)

(7)

Oxybromination of Butenes

In some embodiments, bromo-alkenes (e.g., bromobutenes) may be produced through the oxyhalogenation (e.g., oxybromination) of alkenes (e.g., butenes) using air/oxygen and hydrogen halide (e.g., hydrogen bromide) reactants. Such embodiments avoid the generation of hydrogen halide (e.g., HBr) as a byproduct, thereby reducing the amount of halogen (e.g., bromine) that must be circulated in the operation and eliminating the need to oxidize hydrogen halide to the corresponding halogen (e.g., bromine). For the purposes of brevity and clarity, oxybromination of butenes is described herein with reference to FIG. 4, however, one skilled in the art with the aid of the present disclosure would understand that the method may be applied using other alkenes and/or halogens.

Figure 4:
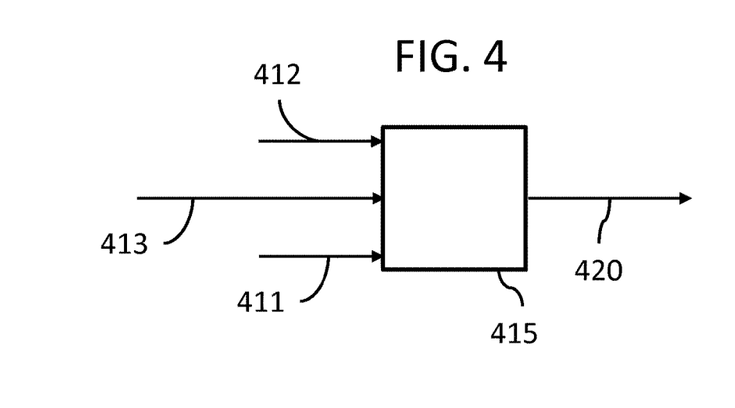
FIG. 4 is a process flow diagram depicting oxybromination of butenes in accordance with one or more embodiments of the present disclosure.

The method may include reacting butenes 412 with hydrogen bromide 413 in the presence of oxygen under reaction conditions sufficient to cause oxybromination of butenes 412 to form an oxybromination product stream that contains bromobutenes 420. For example and without limitation, bromobutenes 420 may be produced through the oxybromination of butenes 412 using air/oxygen 411 and hydrogen bromide 413 as reactants, such as in oxybromination reactor 415. In oxybromination of butenes 412, a molar ratio of butenes/HBr/O$_2$ may range from about 1:0.8:0.6 to about 5:0.8:0.6, for example. The temperature may range from about 275° C. to about 325°, and the residence time may range from about 5 seconds to about 20 seconds. The oxybromination of butenes 412 may occur in the presence of a heterogeneous or homogenous catalyst, such as PdCl$_2$—CuCl$_2$, or TeCl4. Bromobutenes 420 may then be subjected to dehydrobromination, as described herein. While not shown, the product stream of oxybromination reactor 415 that contains bromobutenes 420 may be subjected to separation, such as by distillation, to form a stream enriched in bromobutenes 420 prior to dehydrobromination. Reaction (8) exemplifies oxybromination of butenes 412 using air/oxygen 411 and hydrogen bromide 413 to form bromobutenes 420.

(8)

Bromination of Butenes

In some embodiments, di-halogenated alkanes (e.g., dibromobutanes) may be produced from alkenes (e.g., butenes). For example and without limitation, in embodiments in which the alkene is butenes, the butenes may be produced through conventional means or, for example, through the catalytic dehydrobromination of bromobutanes to butenes as described in U.S. patent application Ser. No. 13/479,085 (discussed above). The alkenes may be reacted with halogen in a halogenation reaction to form the dihalogenated alkanes. For the purposes of brevity and clarity, bromination of butenes is described herein with reference to FIG. 5, however, one skilled in the art with the aid of the present disclosure would understand that the method may be applied using other alkenes and/or halogens.

Figure 5:
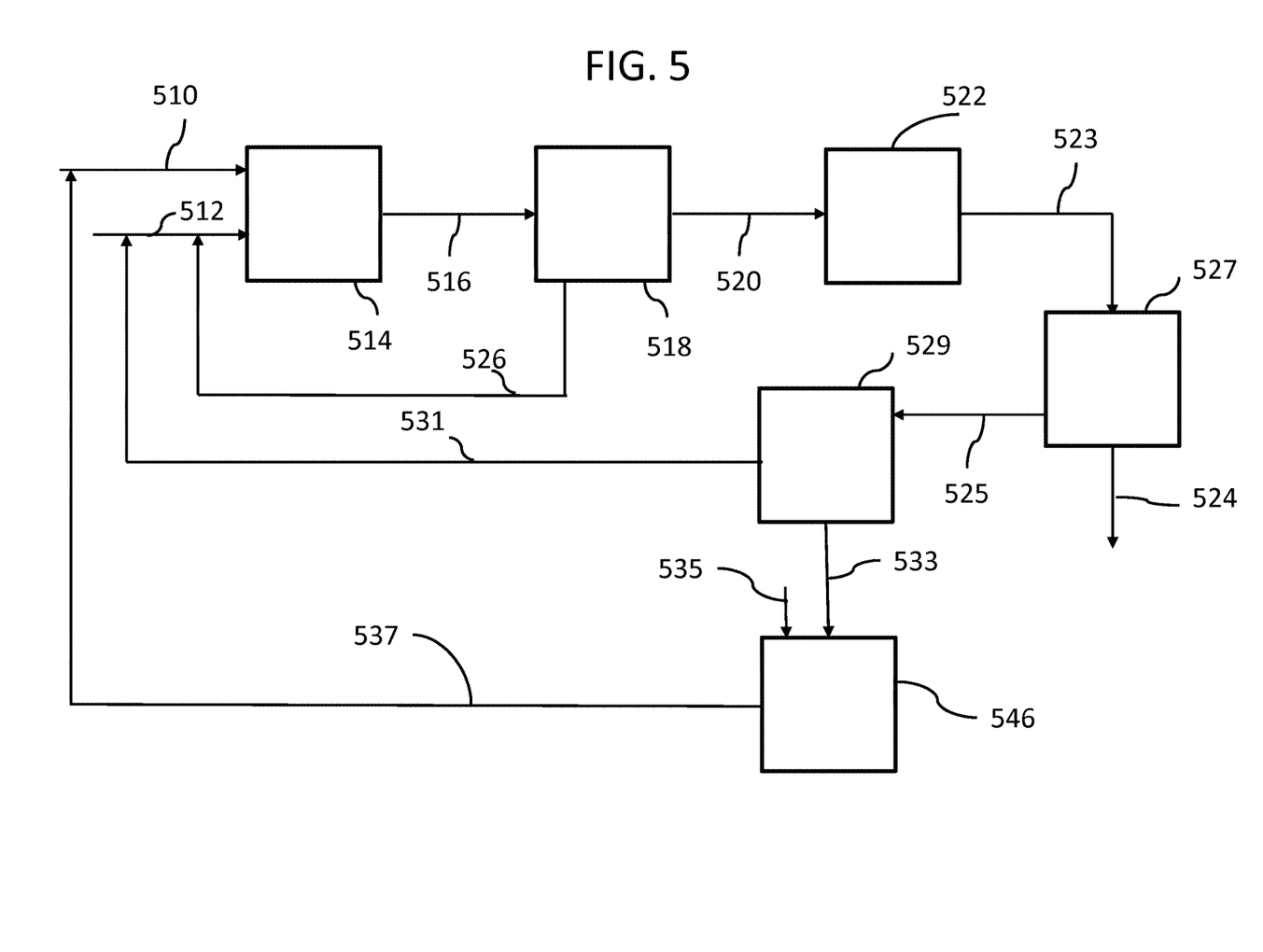
FIG. 5 is a process flow diagram depicting bromination of butenes in accordance with one or more embodiments of the present disclosure.

Production of dibromobutanes 520 from butenes 512 may include reaction of butenes 512 with bromine 510 in a bromination reaction, such as in bromination reactor 514. In the reaction of butenes 512 with bromine 510, the molar ratio of bromine to butenes may range from about 0.75 to about 1.25, or be about 0.95; the temperature may be about ambient, and may range from about 0° C. to about 30° C.; and the residence time may range from about 3 seconds to about 7 seconds, or be about 5 seconds, for example. The reaction of butenes 512 with bromine 510 may be a liquid phase reaction, and may be carried out with no catalyst (i.e., in the absence of a catalyst).

Following bromination, dibromobutanes 520 may be separated from unreacted butenes 526, such as by passing bromination product stream 516 through separator 518 to form a stream enriched in dibromobutanes 520 and a stream enriched in unreacted butenes 526. Bromination product stream 516 may be separated by distillation, for example. Unreacted butenes 526 may be recycled and combined with butene 512 and reintroduced to the bromination reaction upstream of bromination reactor 514.

Dibromobutanes 520 may be dehydrobrominated to form butadienes, such as in dehydrobromination reactor 522, as described in more detail below. Dehydrobromination products stream 523 may be separated in separator 527 to form a stream enriched in butadienes (butadiene product stream 524). Dehydrobromination products stream 523 may be separated by distillation, for example.

Bromobutane 525 present in the dehydrobromination products stream 523 may be separated in separator 527 and subjected to catalytic dehydrobromination in reactor 529 to form butene 531 in the manner as is described in U.S. patent application Ser. No. 13/479,085 (discussed above). Butene 531 may be recycled to bromination reactor 514. HBr 533 produced in reactor 529 may be oxidized in oxidation reactor 546 in the presence of oxygen 535 to produce bromine 537 for reuse in the bromination reaction. Production of dibromobutanes 520 from butenes 512, as exemplified in FIG. 5, may result in the formation of only small amounts of geminal dibromobutanes, such as 0 weight percent geminal dibromobutanes, or less than 1 weight percent geminal dibromobutanes, or less than 0.5 weight percent geminal dibromobutanes, or less than 0.1 weight percent geminal dibromobutanes, or less than 0.05 weight percent geminal dibromobutanes, or less than 0.01 weight percent geminal dibromobutanes. Production of dibromobutanes 520 from butenes 512, as exemplified in FIG. 5, may result in the formation of about 100 weight percent of vicinal 1,2- and 2,3-dibromobutanes, or greater than 99 weight percent vicinal 1,2- and 2,3-dibromobutanes, or greater than 99.9 weight percent vicinal 1,2- and 2,3-dibromobutanes, or greater than 99.99 weight percent vicinal 1,2- and 2,3-dibromobutanes.

Dehydrobromination

Figure 6:
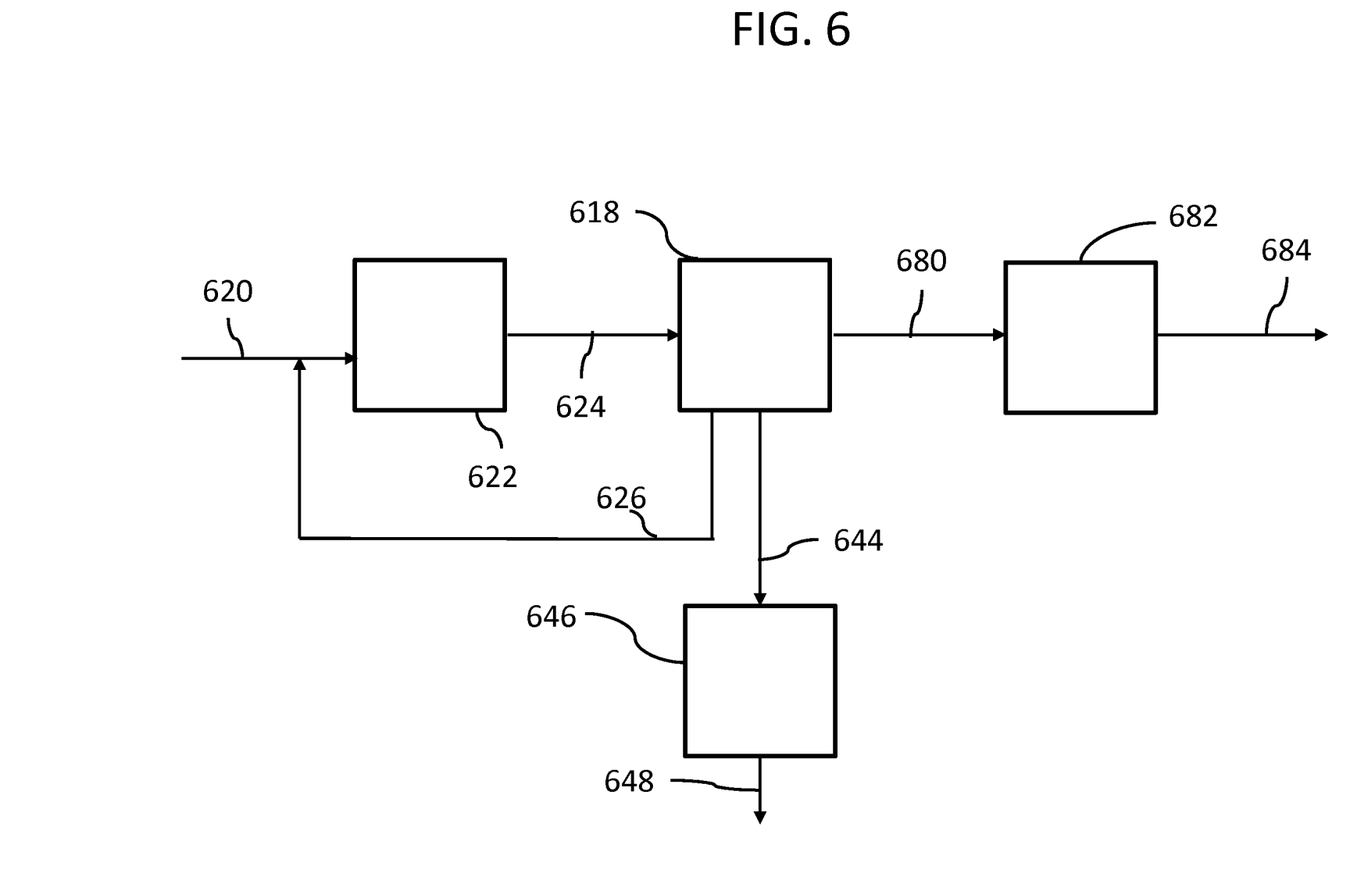
FIG. 6 is a process flow diagram depicting dehydrobromination of alkyl bromide in accordance with one or more embodiments of the present disclosure.

For the purposes of brevity and clarity, dehydrobromination of alkyl bromide is described herein with reference to FIG. 6, however, one skilled in the art with the aid of the present disclosure would understand that the dehydrohalogenation may be applied using other alkyl halides.

Dehydrobromination of alkyl bromide 620 results in the formation of a double bond between a bromine-bearing carbon and the adjacent carbon from which a hydrogen atom is eliminated. Olefins and diolefins may be produced when the dehydrobromination is performed on dibromobutanes, particularly non-geminal dibromobutanes, or on bromobutene. For example and without limitation, alkyl bromide 620 may be dibromobutanes 120 as depicted in FIGS. 1-2B, bromobutenes 320 as depicted in FIG. 3, bromobutenes 420 as depicted in FIG. 4, dibromobutanes 520 as depicted in FIG. 5, or another alky halide as described herein.

The dehydrobromination of alkyl bromide 620 may be performed by an elimination reaction, in which alkyl bromide 620 reacts with a base, which may be dissolved in an alcohol, such as ethanol. The base may be KOH or another alkali hydroxide, for example.

The dehydrobromination may be performed catalytically, such as in dehydrobromination reactor 622. For example and without limitation, dehydrobromination may be performed in the presence of a catalyst that includes silica, sand, silicalite, quartz, titanium dioxide, zirconium dioxide, silicon carbide, stainless steel beads, stainless steel mesh, or metal carbides. In some embodiments, dehydrobromination may be performed thermally, in absence of a catalyst.

Embodiments of the dehydrobromination reaction may form dehydrobromination product stream 624 that includes butadienes, bromobutenes, hydrogen bromide, unconverted dibromobutanes, or combinations thereof. Dehydrobromination product stream 624 may be separated, such as in separator 618. Separation of dehydrobromination product stream 624 may be performed by distillation, for example. Separation of dehydrobromination product stream 624 may form a stream enriched in dibromobutanes and bromobutanes 626, which may be recycled to dehydrobromination reactor 622. Separation of dehydrobromination product stream 624 may form a stream enriched in hydrogen bromide 644. The stream containing hydrogen bromide 644 may be sent to oxidation reactor 646 to regenerate elemental bromine 648, which may be reused in the bromination reactions described herein. Separation of dehydrobromination product stream 624 may form a stream enriched in butadienes 680. Butadienes 680 may include 1,3-butadiene; 1,2-butadiene; 1-butyne; 2-butyne; or combinations thereof.

In some embodiments, butadienes 680 produced in the dehydrobromination reaction are passed over a catalyst to convert 1,2-butadiene; 1-butyne; 2-butyne; or combinations thereof into additional 1,3-butadiene, such as in isomerization reactor 682. Butadienes 680 may be heated when passed over the catalyst. For example, a heated butadiene 680 stream may exit dehydrobromination reactor 622, which may then pass over the catalyst to form a stream enriched in 1,3-butadiene 684. The catalyst may include zeolite, magnesium oxide, Fuller's earth, silica, bentonite, titanium dioxide, or zirconium dioxide, for example. The isomer 1,3-butadiene may be more thermodynamically stable than the isomers 1,2-butadiene; 1-butyne; and 2-butyne, thus, substantially all of the $C_4$ products that are not 1,3-butadiene are converted to 1,3-butadiene when passing over the catalyst (see, Reactions 9 and 10).

$$1,2\text{-butadiene} \rightarrow 1,3\text{butadiene} \tag{9}$$

$$1\text{-butyne}/2\text{-butyne} \rightarrow 1,3\text{butadiene} \tag{10}$$

In some embodiments, the production of butynes may be suppressed by reducing the conversion of geminal dibromides. The extent to which geminal dibromides are converted in the dehydrobromination reaction may be reduced by operating dehydrobromination reactor 622 at a lower temperature.

Hydrogen Bromide Oxidation

Figure 7:
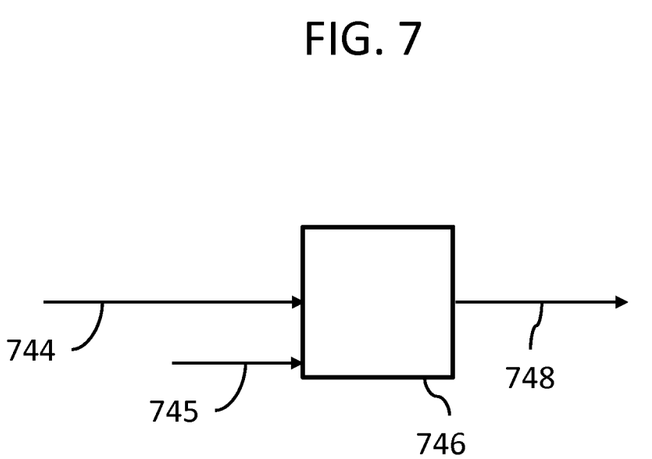
FIG. 7 is a process flow diagram depicting hydrogen bromide oxidation in accordance with one or more embodiments of the present disclosure.

For the purposes of brevity and clarity, oxidation of hydrogen bromide is described herein with reference to FIG. 7, however, one skilled in the art with the aid of the present disclosure would understand that the halogen regeneration may be applied using other hydrogen halides.

Hydrogen bromide 744 may be separated by distillation or other means downstream of bromination, dehydrobromination, or both, as described above. The separated hydrogen bromide 744 may then be sent to oxidation reactor 746 in which hydrogen bromide 744 is oxidized with air/oxygen 745 over a catalyst to regenerate elemental bromine 748 for optional reuse in the bromination reactions described herein. Oxidation of hydrogen bromide 744 also forms water (not shown). For example and without limitation, hydrogen bromide 744 may be hydrogen bromide 144, 144a, 144b, 140, 533 or 644, as shown in FIGS. 1-6.

The catalyst used in oxidation reactor 746 may be a chromium or cerium oxide-based catalyst, for example, to produce bromine and water. In some embodiments, the initiation temperature for oxidation of hydrogen bromide 744 is approximately 200° C., while the maximum stable operating temperature for the catalyst is approximately 850° C. Hydrogen bromide 744 oxidation is a highly exothermic reaction and may be carried out using a reactor system, such as an isothermal reactor or a multiple stage adiabatic reactor system with intermediate cooling using quench and/or heat exchangers. Examples of such systems may be found in U.S. Pat. No. 7,883,568, issued Feb. 8, 2011, which is incorporated fully herein by reference.

The above examples demonstrate possible embodiments of the present disclosure. While the foregoing is directed to embodiments, versions and examples, which are included to enable a person of ordinary skill in the art to make and use the inventions when the information in this patent is combined with available information and technology, the disclosure is not limited to only these particular embodiments, versions and examples. Other and further embodiments, versions and examples may be devised without departing from the basic scope thereof and the scope thereof is determined by the claims that follow.

What is claimed is:

1. A method comprising:
   reacting n-butane with bromine in one or more bromination reactors to form a bromination product stream rich in dibromobutanes; and
   subjecting the dibromobutanes to dehydrobromination in a dehydrobromination reactor to form a dehydrobromination product stream comprising 1,3-butadiene and HBr.

2. The method of claim 1, wherein the n-butane is converted to a dibromobutane in a single step.

3. The method of claim 1, wherein the one or more bromination reactors includes a first bromination reactor and a second bromination reactor, wherein the second bromination reactor is downstream of the first bromination reactor, wherein monobromobutane is formed in the first bromination reactor by reaction of the n-butane with the bromine, and wherein the dibromobutane is formed in the second bromination reactor by reaction of the monobromobutane with the bromine.

4. The method of claim 3, wherein the reaction conditions in the first bromination reactor are different than the reaction conditions in the second bromination reactor.

5. The method of claim 3, wherein the reaction conditions in the first bromination reactor are the same as the reaction conditions in the second bromination reactor.

6. The method of claim 3, forming a stream enriched in unreacted bromobutanes, combing the stream enriched in unreacted bromobutanes with the monobromobutane upstream of the second bromination reactor.

7. The method of claim 3, wherein a first bromination product stream is formed in the first bromination reactor and a second bromination product stream is formed in the second bromination reactor, and wherein the method further comprises subjecting the first bromination product stream to a separation upstream of the second bromination reactor to form a stream enriched in monobromobutanes.

8. The method of claim 1 further comprising forming a stream enriched in polybromobutanes;
   hydrogenating the stream enriched in polybromobutanes to form a hydrogenated products stream comprising butane, bromobutanes, additional dibromobutanes, and hydrogen bromide;
   separating the hydrogenated products stream to form a stream comprising the butane and the bromobutanes, a stream comprising the hydrogen bromide, and a stream comprising the additional dibromobutanes;
   recycling the stream comprising the butane and the bromobutanes to combine with the n-butane upstream of the bromination reactor;
   combining the stream comprising the additional dibromobutanes with the dibromobutanes upstream of the dehydrobromination reactor; and
   subjecting the stream comprising the hydrogen bromide to oxidation to form elemental bromine and water, wherein the elemental bromine is recycled to combine with the bromine upstream of the bromination reactor.

9. The method of claim 1 further comprising forming a stream enriched in hydrogen bromide; and
   subjecting the stream enriched in hydrogen bromide to oxidation to form elemental bromine and water, wherein the elemental bromine is recycled to combine with the bromine upstream of the bromination reactor.

10. The method of claim 1 further comprising forming a stream enriched in unreacted butane, butyl bromides, or combinations thereof; and
    recycling the stream enriched in unreacted butane, butyl bromides, or combinations thereof to combine with the n-butane upstream of the bromination reactor.

11. The method of claim 1, further comprising separating the dehydrobromination product stream to form a stream enriched in butadienes.

12. The method of claim 11, wherein separating the dehydrobromination product stream forms a stream comprising hydrogen bromide, and wherein the method further comprises subjecting the hydrogen bromide to oxidation to form elemental bromine.

13. The method of claim 1, wherein the dehydrobromination product stream further comprises 1,2-butadiene, 1-butyne, 2-butyne, or combinations thereof; and
    wherein the method further comprises passing the dehydrobromination product stream over a catalyst to convert 1,2-butadiene, 1-butyne, 2-butyne, or combinations thereof into additional 1,3-butadiene.

14. The method of claim 13, wherein the catalyst comprises zeolite or magnesium oxide.

15. The method of claim 1, wherein the dehydrobromination is performed in the presence of a catalyst comprising silica, sand, silicalite, quartz chips, titanium dioxide, zirconium dioxide, silicon carbide, stainless steel beads, stainless steel mesh, or metal carbides.

16. The method of claim 1, wherein the method exhibits a carbon loss due to coking or incineration of undesired byproducts that is below 10 wt. % of the starting n-butane.

17. The method of claim 1, wherein the bromination is performed in the presence of a polar surface catalyst.

18. The method of claim 17, wherein the polar surface catalyst comprises silica, glass, quartz chips, silicalite, zirconia or titania.

19. A method comprising:
reacting butene with bromine in a bromination reactor under reaction conditions adapted for selective bromination of the butene in the allylic position to form a bromination product stream comprising bromobutenes; and
subjecting the bromobutenes to dehydrobromination to form a dehydrobromination product stream comprising 1,3-butadiene.

20. The method of claim 19, wherein the bromobutenes are subjected to dehydrobromination in a dehydrobromination reactor downstream of the bromination reactor.

21. The method of claim 19, wherein the bromobutenes are subjected to dehydrobromination in the bromination reactor to form the dehydrobromination product stream comprising 1,3-butadiene in situ.

22. The method of claim 19, wherein the butenes and the bromine are both preheated and mixed together prior to reacting in the bromination reactor.

23. The method of claim 22, wherein the butenes and the bromine are both preheated to a temperature of exceeding 250° C.

24. A method comprising:
reacting butene with hydrogen bromide in the presence of oxygen in an oxybromination reactor under reaction conditions sufficient to cause oxybromination of the butenes to form an oxybromination product stream comprising bromobutenes; and
subjecting the bromobutenes to dehydrobromination in a dehydrobromination reactor to form a dehydrobromination product stream comprising 1,3-butadiene.

25. A method comprising:
reacting butene with bromine in a bromination reactor to form a bromination product stream rich in vicinal dibromobutanes; and
subjecting the dibromobutanes to dehydrobromination in a dehydrobromination reactor to form a dehydrobromination product stream comprising 1,3-butadiene and HBr.

26. The method of claim 25, further comprising:
forming a stream enriched in unreacted butenes; and
recycling the stream enriched in unreacted butenes to combine with the butene upstream of the bromination reactor.

27. The method of claim 25, further comprising separating the dehydrobromination product stream to form a stream enriched in butadienes and a stream enriched in bromobutanes.

28. The method of claim 27, further comprising:
subjecting the stream enriched in bromobutanes to catalytic dehydrobromination to form a stream comprising butene and a stream comprising hydrogen bromide;
recycling the stream comprising butene to combine with the butene upstream of the bromination reactor;
subjecting the stream comprising hydrogen bromide to oxidation to form element bromine; and
recycling the element bromine to combine with the bromine upstream of the bromination reactor.

* * * * *